United States Patent [19]
Koga et al.

[11] Patent Number: 5,532,408
[45] Date of Patent: Jul. 2, 1996

[54] α-CHAIN-MODIFIED ISOCARBACYCLINS AND PROCESS FOR THE PRODUCTION THEREOF

[75] Inventors: Masahiro Koga; Toshio Tanaka, both of Iwakuni; Takao Fujii, Koganei; Tsukio Masegi, Hino, all of Japan

[73] Assignee: Teijin Limited, Osaka, Japan

[21] Appl. No.: 411,649

[22] PCT Filed: Oct. 1, 1993

[86] PCT No.: PCT/JP93/01407

§ 371 Date: Apr. 5, 1995

§ 102(e) Date: Apr. 5, 1995

[87] PCT Pub. No.: WO94/07838

PCT Pub. Date: Apr. 14, 1995

[30] Foreign Application Priority Data

Oct. 5, 1992 [JP] Japan .................................. 4-266084

[51] Int. Cl.$^6$ ............. C07C 62/06; C07C 69/74; C07C 177/00; C07F 7/04
[52] U.S. Cl. ............. 562/466; 562/501; 562/503; 562/504; 562/506; 560/56; 560/119; 556/441
[58] Field of Search .................. 562/466, 501, 562/503, 504, 506; 560/56, 119; 556/441

[56] References Cited

PUBLICATIONS

Lautens, M. et al J.ACS 1995 117 1954–1964.

*Primary Examiner*—Paul J. Killos
*Attorney, Agent, or Firm*—Sherman and Shalloway

[57] ABSTRACT

Provided are α-chain-modified isocarbacyclins of which the α-chain is modified with a phenylene group, a cycloalkylene group or a thiophendiyl group, and these α-chain-modified isocarbacyclins show the activity for inhibiting the DNA synthesis of human smooth muscle cell and are expected to be capable of inhibiting the hypertrophy of a blood vessel.

4 Claims, 1 Drawing Sheet

α-CHAIN-MODIFIED ISOCARBACYCLINS AND PROCESS FOR THE PRODUCTION THEREOF

This application is a 371 PCT of JP93/01407 filed Oct. 1, 1993.

TECHNICAL FIELD

The present invention relates to α-chain-modified isocarbacyclins and a process for the production thereof. More specifically, it relates to a process for positionally selective production of α-chain-modified isocarbacyclins having oxygen atoms in the 6,9α-positions of prostaglandin $I_2$ replaced with methine group (—CH=) and having an optionally substituted phenylene group in the α-chain from 2,6,7-trisubstituted-3-methy-lenebicyclo[3.3.0]-oct as starting materials, and α-chain-modified isocarbacyclins that can be produced by the above process.

TECHNICAL BACKGROUND

Prostacyclin is a topical hormone produced mainly in the inner wall of the arterial blood vessel of a living body, and is an important factor which adjusts the cellular functions of a living body with its strong physiological activities such as platelet aggregation inhibition activity and vasodilation activity. Attempts have been made to provide this directly as a drug (Clinical Pharmacology of Prostacyclin, Raven Press, N.Y. 1981).

However, natural prostacyclin has an extremely easily hydrolyzable enol ether bond in its molecule so that it is easily hydrolyzed under neutral or acidic conditions to be deactivated. Natural prostacyclin, therefore, cannot be said to be a desirable compound as a drug due to its chemical instability. Under the circumstances, studies have been and are being diligently made of chemically stable synthetic prostacyclin derivatives having physiological activities similar to those of natural prostacyclin.

JP-A-57-54180 and EP 0 045842B1 corresponding thereto disclose prostacylins of the following formula,

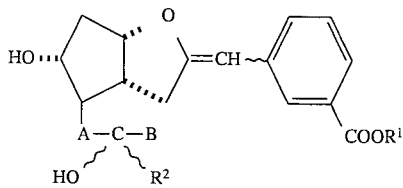

wherein $R^1$ is a H, a pharmaceutically acceptable cation or an alcohol residue, $R^2$ is H or $CH_3$, A is —$CH_2CH_2$—, (trans)—CH=CH— or —C≡C— and B is an alkyl group represented by

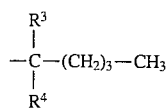

(each of $R^3$ and $R^4$ is H, $CH_3$ or $C_2H_5$) or a cyclohexyl group, and it is disclosed that these prostacyclins have activities similar to those of prostacyclin on the aggregation of platelet and blood pressure but that these prostacyclins have higher stability than prostacyclin.

JP-A-3-7275 and EP 0 389162A1 corresponding thereto disclose prostacyclins of the following formula,

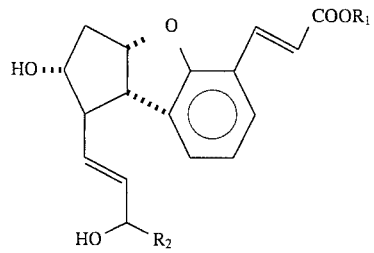

wherein $R_1$ is H, a pharmaceutically acceptable cation or an ester residue and $R_2$ is a $C_{1-12}$ linear alkyl group or the like, that is, 2,5,6,7-tetranor-4,8-inter-m-phenylene $PGI_2$ derivatives, and it is disclosed that these prostacyclins have excellent stability in a living body.

JP-A-2-57548 discloses prostacyclins of the following formula,

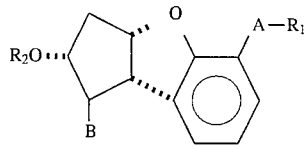

wherein $R_1$ is —$COOR_2$ ..., $R_2$ is H or a pharmaceutically acceptable cation, A is —$(CH_2)_n$— (n=an integer of 1 to 3), —CH=CHCH$_2$—, —CH$_2$CH=CH— or —CH$_2$OCH$_2$— and B is, for example,

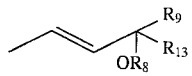

($R_8$ is H, $C_{1-12}$ acyl or the like, $R_9$ is H or $C_{1-4}$ alkyl and $R_{13}$ is $C_{5-10}$ branched alkyl or the like), and it is disclosed that these prostacyclins have the activities such as the inhibition of platelet aggregation and the reduction of blood pressure, Further, it is known that prostacyclin derivatives having the oxygen atoms in the 6,9-αpositions of prostacyclin replaced with methine group, i.e., 9(O)-methanoprostacyclin (carbacyclin) is a prostacyclin derivative which satisfies chemical stability (see Prostacyclin, I. R. Vane and S. Bergstrom. Eds. Raven Press, N.Y., pages 31 to 34), and this derivative is expected to be applied as a drug.

U.S. Pat. No. 4,306,076 discloses carbacyclins of the following formula,

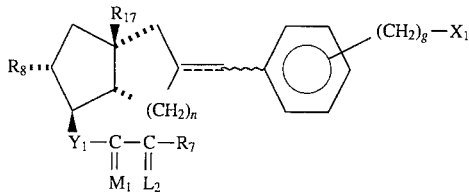

wherein g is 0, 1, 2 or 3, n is 1 or 2, $L_1$ is α-$R_3$,β-$R_4$; α-$R_4$,β-$R_3$ or a mixture of these (each of $R_3$ and $R_4$ is H, $CH_3$ or F), $M_1$ is α-OH,β-$R_5$ or α-$R_5$,β-OH ($R_5$ is H or $CH_3$), $R_7$ is —$C_mH_{2m}$—$CH_3$ (m is an integer of 1 to 5) or the like, $Y_1$ is trans—CH=CH—, cis—CH=CH—, —CH$_2$CH$_2$— or —C≡C—, X$_1$ is —COOR$_1$ (R$_1$ is H, C$_{1-12}$ alkyl or the like), R$_8$ is OH, CH$_2$OH or H and R$_{17}$ is H or a C$_{1-4}$ alkyl group, and it is disclosed that these carbacyclins are useful as an antithrombotic agent, an antiulcer agent and an antasthmatic.

JP-A-58-92637 discloses carbacyclins of the following formula,

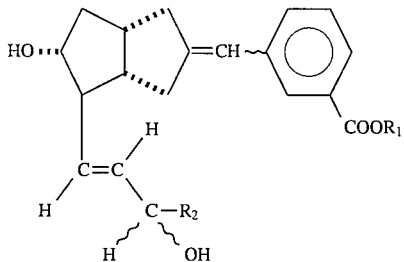

wherein

R$_1$ is H, a C$_{1-4}$ alkyl group or a pharmaceutically harmless cation, and R$_2$ is a cyclohexyl group, a 4-methylcyclohexyl group or a 1-adamantyl group, and it is disclosed that these carbacyclins are useful for inhibiting the aggregation of platelet.

JP-A-58-126835 and EP 0 080718A1 corresponding thereto disclose prostacyclins and carbacyclins of the following formula,

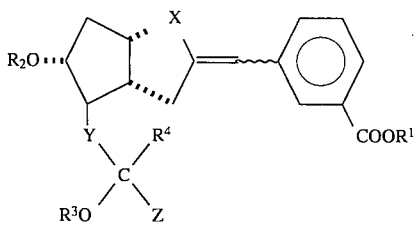

wherein

R$^1$ is H, C$_{1-4}$ alkyl, a pharmaceutically acceptable ammonium cation or a metal cation, each of R$^2$ and R$^3$ is independently H or a protective group such as alkanoyl, R$^4$ is H or C$_{1-4}$ alkyl, X is —O— or —CH$_2$—, Y is —C≡C— or trans—CH=CW— (W is U, Br or F) and Z is C$_{6-9}$ alkyl optionally substituted with one or two Fs or C$_{1-4}$ alkyls, or optionally substituted arylmethyl or aryloxymethyl, and it is disclosed that these compounds enhance the platelet aggregation activity and reduce the anti-hypertension activity.

International Patent Publication WO 83/04021 discloses carbacyclins of the following formula,

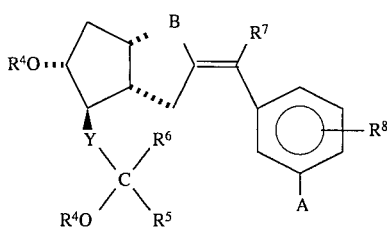

wherein

A is carboxy, cyano, tetrazolyl, —COOR$_3$ (R$^3$ is C$_{1-4}$ alkyl or a pharmaceutically acceptable cation) or —CONR$^1$ R$^2$ (each of R$^1$ and R$^2$ is H, phenyl, C$_{1-5}$ alkyl or C$_{1-4}$ alkylsulfonyl, or R$^1$ and R$^2$ may form together a C$_{3-6}$ α, ω-alkylene group), B is —O— or —CH$_2$—, Y is vinylene optionally substituted Br or —C≡C—, R$^4$ is H or tetrahydropyran-2-yl, R$^5$ is C$_{5-9}$ alkyl optionally interrupted by 1 or more oxygen atoms, —CH=CH—, —C≡C—, phenoxymethyl optionally substituted with halogen or trifluoromethyl or C$_{3-5}$ alkenyloxymethyl, R$^6$ is H or C$_{1-4}$ alkyl, R$^7$ is H, halogen, cyano, C$_{1-4}$ alkyl or C$_{1-4}$ alkoxy, and R$^8$ is H, halogen, cyano, nitro, hydroxy or C$_{2-5}$ alkanoylamide, provided that, when R$^5$ is C$_{5-9}$ alkyl not substituted or not interrupted by any oxygen atom, —CH=CH—, —C≡C— or phenoxymethyl optionally substituted with halogen or trifluoromethyl, either R$^7$ or R$^8$ is other than H, or A is other than carboxy and —COOR$^3$, and it is disclosed that these carbacyclins show cellular protection, aggregation inhibition and low hypotension activities and are of an activity-sustaining type.

German Patent Laid-Open Publication DE 3408699A1 discloses carbacyclins of the following formula,

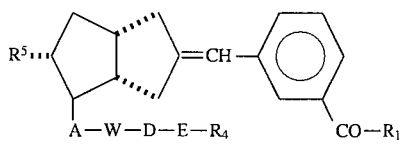

wherein

R$_1$ is OR$_2$ or R$_3$ (R$_2$ is H, C$_{1-10}$ alkyl, C$_{5-6}$ cycloalkyl or the like, and R$_3$ is C$_{1-10}$ alkyl or the like), A is —CH$_2$CH$_2$—, trans—CH=CH— or —C≡C—, W is

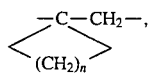

or a functional derivative of any one of these, D is $$-\overset{}{\underset{(CH_2)_n}{C}}-CH_2-,$$

a C$_{1-3}$ linear saturated alkylene group or a C$_{2-5}$ branched saturated, or linear or branched unsaturated alkylene group, n is 1, 2 or 3, E is —C≡C— or —CR$_6$—CR$_7$— (each of R$_6$ and R$_7$ is independently H, C$_{1-5}$ alkyl or halogen), or when R$_1$ is R$_3$, E is —CH$_2$CH$_2$—, R$_4$ is C$_{1-10}$ alkyl, C$_{3-10}$ cycloalkyl, and R$^5$ is a hydroxyl group optionally protected.

Finally, JP-A-2-295950 and EP 0396024A2 corresponding thereto disclose prostacyclin and carbacyclin of the following formula,

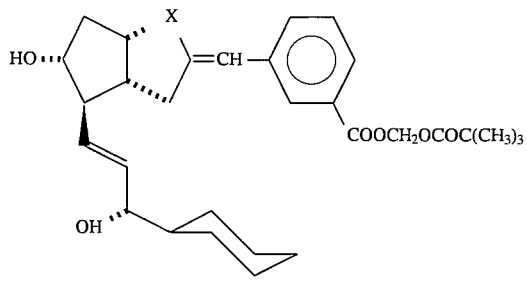

wherein

X is —O— or —CH$_2$—, and it is also disclosed that these compounds show the oral-absorption property suitable for oral administration.

Meanwhile, a compound which shows the activity for the inhibition of the hypertrophy of a blood vessel is useful, for example, as a drug for inhibiting the hypertrophy and occlusion of a blood vessel caused mainly by the proliferation of blood vessel smooth muscle cells after various angioplastic operations, arterial bypass operations and internal organic transplantation, as a drug for the prevention and therapy of blood vessel hypertrophy and occlusion (or a drug for the inhibition of the proliferation of blood vessel smooth muscle cells) and further as a drug for the prevention and therapy of arterial sclerosis.

However, it has not been reported that prostacyclin or its derivatives have the activity for inhibiting the blood vessel hypertrophy.

DISCLOSURE OF THE INVENTION

It is an object of the present invention to provide novel isocarbacyclins.

It is another object of the present invention to provide α chain-modified novel isocarbacyclins.

It is further another object of the present invention to provide isocarbacyclins which show the activity for inhibiting blood vessel hypertrophy by preventing the DNA synthesis of smooth muscle cells.

It is further another object of the present invention to provide an industrially advantageous process for producing the α-chain-modified isocarbacyclins of the present invention.

Other objects and advantages of the present invention will be apparent from the following description.

According to the present invention, the above objects and advantages of the present invention are achieved, first, by α-chain-modified isocarbacyclins of the following formula (1),

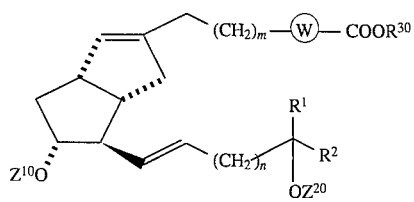

wherein (W) is a phenylene group, a $C_3$–$C_7$ cycloalkylene group or a thiophendiyl group;

$R^1$ is a hydrogen atom, a methyl group, an ethyl group or a vinyl group;

$R^2$ is a linear or branched $C_3$–$C_8$ alkyl group, alkenyl group or alkynyl group or a $C_3$–$C_7$ cycloalkyl group;

$R^{30}$ is a hydrogen atom, a $C_1$–$C_{10}$ alkyl group, a phenyl group, a benzyl group, a naphthyl group or one equivalent of a cation;

each of $Z^{10}$ and $Z^{20}$ is independently a hydrogen atom, tri($C_1$–$C_7$ hydrocarbon)silyl group or a group which forms an acetal bond or an ester bond together with an oxygen atom to which it bonds;

n is 0 or 1; and m is an integer of 0 to 4.

Further, according to the present invention, as a process for the production of the above α-chain-modified isocarbacyclins of the present invention, there is provided a process for the production of α-chain-modified isocarbacyclins of the above formula (1), which comprises reacting 2,6,7-trisubstituted-3-methylenebicyclo[3.3.0]octanes of the following formula (2),

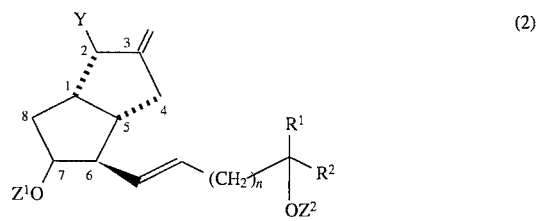

wherein

Y is a group of

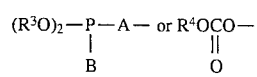

(in which each of $R_3$s is independently a $C_1$–$C_6$ hydrocarbon group, A and B are both oxygen atoms or one is an oxygen atom and the other is a sulfur atom, and $R^4$ is a $C_1$–$C_6$ hydrocarbon group);

$R^1$ is a hydrogen atom, a methyl group, an ethyl group or a vinyl group;

$R^2$ is a linear or branched $C_3$–$C_8$ alkyl group, alkenyl group or alkynyl group, or a $C_3$–$C_7$ cycloalkyl group;

each of $Z^1$ and $Z^2$ is independently a tri($C_1$–$C_7$ hydrocarbon)silyl group or a group which forms an acetal bond or an ester bond together with an oxygen atom to which it bonds; and n is 0 or 1, with an organic zinc compound of the following formula (3), $$X^1Zn-(CH_2)_m-(W)-COOR^3 \quad (3)$$

wherein $R^3$ is a $C_1$–$C_{10}$ alkyl group, a phenyl group, a benzyl group or a naphthyl group;

(W) is a phenylene group, a $C_3$–$C_7$ cycloalkylene group or a thiophendiyl group;

$X^1$ is a halogen atom, and m is an integer of 0 to 4, in the presence of a cuprous salt of the following formula (4), $$CuX^2tm \quad (4)$$

wherein $X^2$ is a cyano group or a halogen atom, optionally subjecting the reaction product to a deprotection reaction and further optionally subjecting the reaction product to a salt-forming reaction.

PREFERRED EMBODIMENTS OF THE INVENTION

Figure 1:
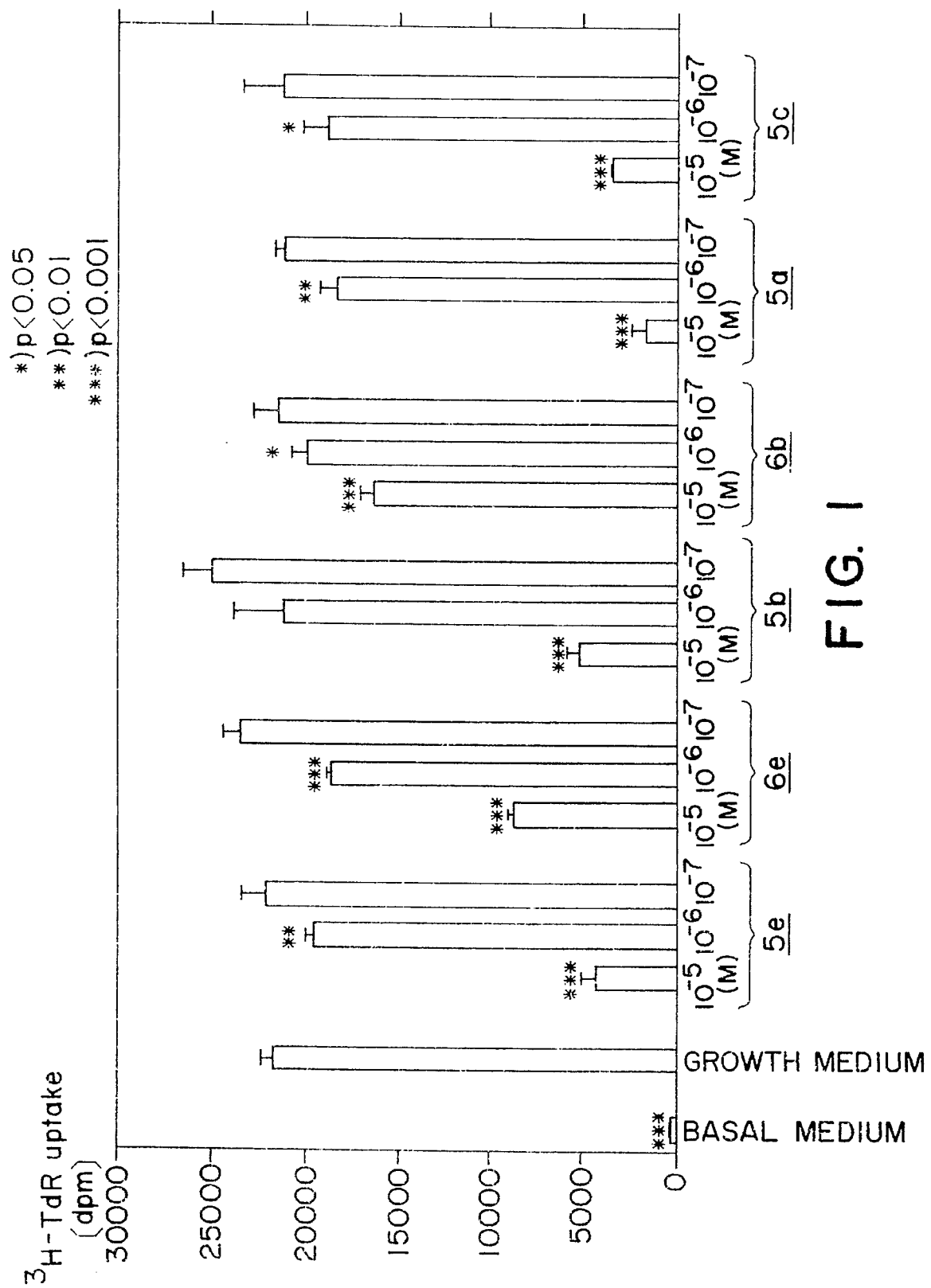
FIG. 1 shows the results of measurement of some of the compounds of the present invention for the activity for the inhibition of DNA synthesis of human smooth muscle cells.

First of all, the above process for the production of the present invention will be explained hereinafter.

The starting material used in the process of the present invention is 2,6,7-trisubstituted-3-methylenebicyclo[3.3.0] octanes of the above formula (2) and the organic zinc compound of the above formula (3).

In the above formula (2), Y is a substituent of $(R^3O)_2P(=B)A-$ or $R^4OC(=O)O-$. In the substituent $(R^3O)_2P(=B)A-$, $R^3$ is a $C_1-C_6$ hydrocarbon group. A and B are both oxygen atoms, or one of A and B is an oxygen atom and the other is a sulfur atom. In the substituent $R^4OC(=O)O-$, $R^4$ is a $C_1-C_6$ hydrocarbon group. $R^1$ is a hydrogen atom, a methyl group, an ethyl group or a vinyl group. $R^2$ is a linear or branched $C_3-C_8$ alkyl group, alkenyl group or alkynyl group, or a $C_3-C_7$ cycloalkyl group. $Z^1$ and $Z^2$ are the same or different, and each is a tri($C_1-C_7$ hydrocarbon)silyl group or a group to form an acetal bond or an ester bond together with an oxygen atom to which it bonds.

In the substituent $(R^3O)_2P(=B)A-$ represented by Y, examples of the $C_1-C_6$ hydrocarbon group as $R^3$ include methyl, ethyl, propyl and phenyl groups. Examples of Y preferably include diethoxyphosphoryloxy, dipropoxyphosphoryloxy, diphenoxyphosphoryloxy, dimethoxythiophosphoryloxy, diethoxythiophosphoryloxy, dimethoxyphosphorylthio and diethoxyphosphorylthio groups.

In the substituent $R^4OC(=O)O-$ represented by Y, examples of the $C_1-C_6$ hydrocarbon group as $R^4$ include methyl, ethyl, propyl, allyl, butyl, hexyl and phenyl groups. Examples of Y preferably include those corresponding to $R^4$ such as methoxycarbonyloxy.

$R^1$ is a hydrogen atom, a methyl group, an ethyl group or a vinyl group.

Examples of the linear or branched $C_3-C_8$ alkyl group as $R^2$ include n-propyl, n-butyl, n-pentyl, n-hexyl, n-heptyl, n-octyl, 1-methylpentyl, 1-methylhexyl, 1,1-dimethylpentyl, 2-methylpentyl, 2-methylhexyl, 5-methylhexyl and 2,5-dimethylhexyl. Of these, preferred are n-butyl, n-pentyl, n-hexyl, (R)- or (S)- or (RS)-1-methylpentyl and (R)- or (S)- or (RS)-2-methylhexyl groups.

Examples of the linear or branched $C_3-C_8$ alkenyl group as $R^2$ include 2-butenyl, 2-pentenyl, 3-pentenyl, 2-hexenyl, 4-hexenyl, 2-methyl-4-hexenyl and 6-methyl-5-heptenyl groups.

Examples of the linear or branched $C_3-C_8$ alkynyl group as $R^2$ include 2-butynyl, 2-pentynyl, 3-pentynyl, 2-hexynyl, 4-hexynyl, 2-octynyl, 1-methyl-3-pentynyl, 1-methyl-3-hexynyl and 2-methyl-4-hexynyl.

Examples of the $C_3-C_7$ cycloalkyl group as $R^2$ include cyclopropyl, cyclobutyl, cyclopentyl, cyclohexyl, cycloheptyl, cyclooctyl and cyclodecyl groups. Of these, preferred are cyclopentyl and cyclohexyl groups.

Examples of the tri($C_1-C_7$ hydrocarbon)silyl group as $Z^1$ and $Z^2$ preferably include tri($C_1-C_4$ alkyl)silyl groups such as trimethylsilyl, triethylsilyl, triisopropylsilyl and t-butyldimethylsilyl groups; diphenyl($C_1-C_4$ alkyl)silyl groups such as t-butyldiphenylsilyl group; di($C_1-C_4$ alkyl)phenylsilyl groups such as a dimethylphenylsilyl group and a tribenzylsilyl group. Tri($C_1-C_4$ alkyl)silyl and diphenyl($C_1-C_4$ alkyl)silyl groups are preferred, and above all, a t-butyldimethylsilyl group is particularly preferred.

Examples of the group to form an acetal bond together with the oxygen atom to which it bonds include methoxymethyl, 1-ethoxyethyl, 2-methoxy-2-propyl, 2-ethoxy-2-propyl, (2-methoxyethoxy)methyl, benzyloxymethyl, 2-tetrahydropyranyl and 2-tetrahydrofuranyl groups. 2-Tetrahydropyranyl, 2-tetrahydrofuranyl, 1-ethoxyethyl, 2-ethoxy-2-propyl and (2-methoxyethoxy)methyl groups are preferred, and of these, 2-tetrahydropyranyl group is particularly preferred.

Examples of the group to form an ester bond together with the oxygen atom to which it bonds include $C_1-C_5$ acyl groups such as formyl, acetyl, propionyl, butanoyl and pentanonyl groups, a benzoyl group and a toluyl group. Acetyl and benzoyl groups are particularly preferred.

In the above formula (2), n is 0 or 1. When n is 0, the above formula (2) represents 2,6,7-trisubstituted-3-methylenebicyclo[3.3.0]octanes of the following formula (2)-1,

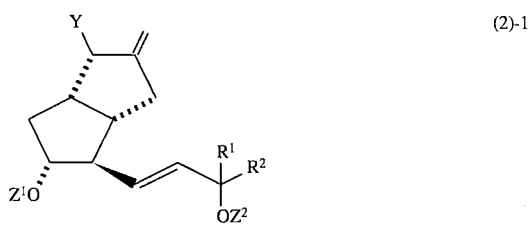

wherein $R^1$, $R^2$, $Z^1$, $Z^2$ and Y are as defined above.

When n is 1, the above formula (2) represents 2,6,7-trisubstituted-3-methylenebicyclo[3.3.0]octanes of the following formula (2)-2,

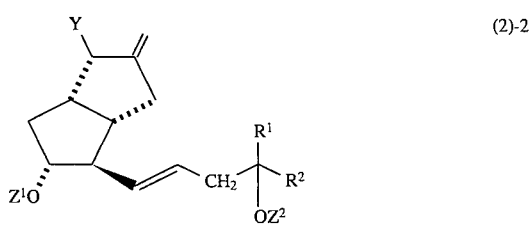

wherein $R^1$, $R^2$, $Z^1$, $Z^2$ and Y are as defined above.

Some of the 2,6,7-trisubstituted-3-methylenebicyclo [3.3.0]octanes of the above formula (2) [including the formulae (2)-1 and (2)-2)] used as starting materials in the present invention are known and they are produced by the following synthesis schemes (Scheme I).

Scheme I

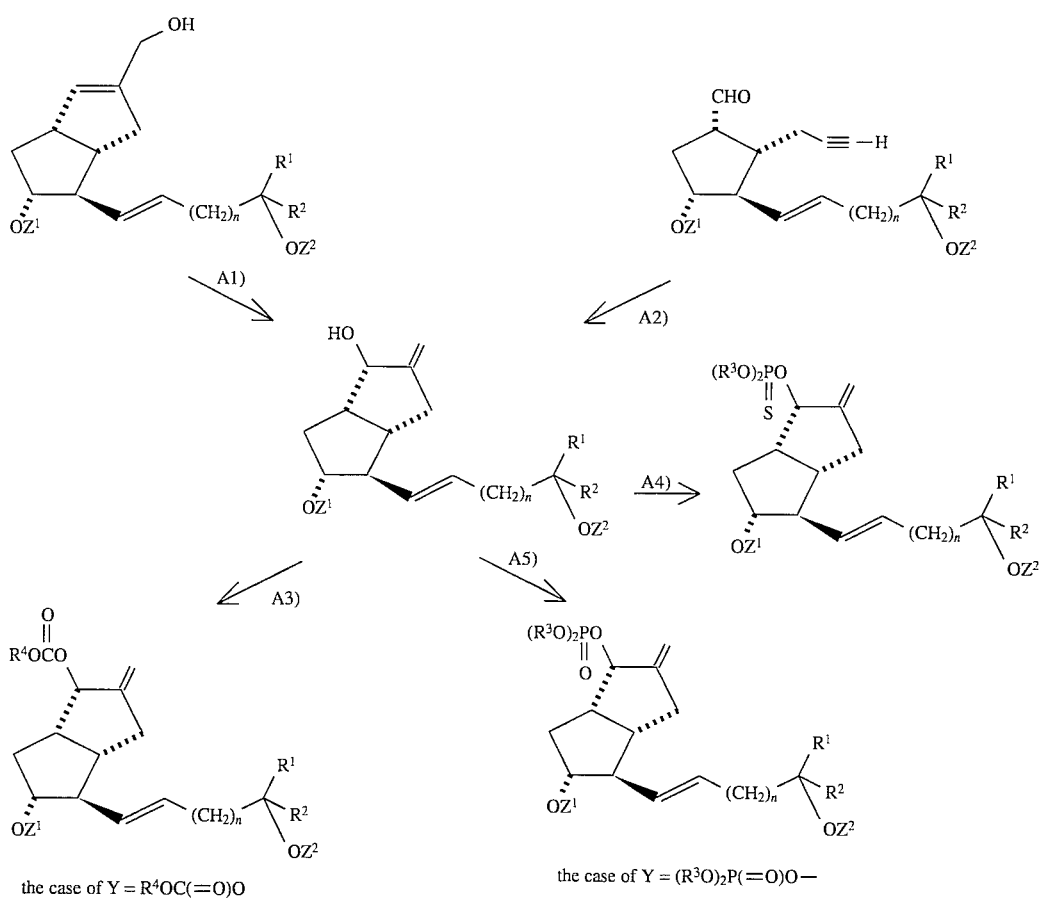

In the above Scheme I, the steps A1) to A5) are described in the following Japanese Laid-open Patent Publications and known per se:

Step A1) JP-A-62-61937

Step A2) JP-A-62-258330

Step A3) JP-A-63-303956

Step A4) JP-A-62-61937

Step A5) JP-A-62-61937

The 2,6,7-trisubstituted-3-methylenebicyclo[3.3.0]octanes of the formula (2) in which Y is $(R^3O)_2P(=O)S-$ can be produced by the following synthesis scheme (Scheme II).

Scheme II

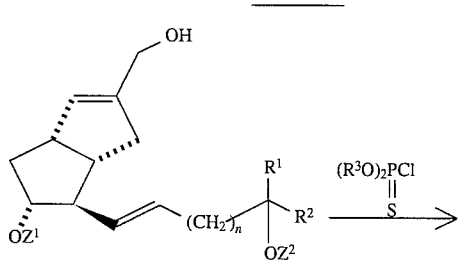

-continued
Scheme II

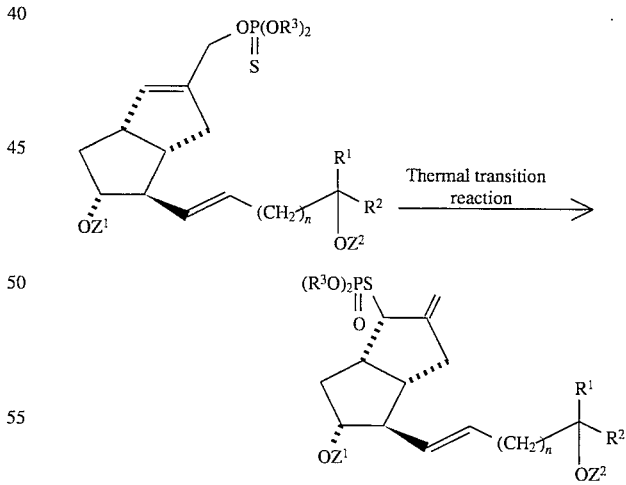

In the above formula (2), the carbon atom to which $R^1$, $R^2$ and $OZ^2$ bond are asymmetric carbon, while R-form, S-form and a mixture of these in any proportions may be included.

Those 2,6,7-trisubstituted-3-methylenebicyclo[3.3.0]octanes of the above formula (2) which are identical to the skeleton of natural prostacyclin in the steric configuration of a bicyclo-ring and the steric configuration of the 6,7-positions are particularly useful steric isomers. While, in the production process of the present invention, steric isomers that can be present due to different steric isomerism in each position and a mixture of these in any proportions are included. Further, the production process of the present invention can give the same product from steric isomers in the position to which Y in the 2-position bonds, and these steric isomers can be equally starting materials.

Typical specific examples of the 2,6,7-trisubstituted-3-methylenebicyclo[3.3.0]octanes of the above formula (2) used as raw materials will be listed below, while derivatives which are elementary compounds in which Y. $Z^1$ and $Z^2$ are hydrogen atoms will be described first.

(001) (1S,5R,6R,7R)-3-methylene-6-[(E,3S)-3-hydroxy-1-octenyl]-7-hydroxybicyclo[3.3.0]octane, (002) (1S,5R,6R,7R)-3-methylene-6-[(E,3S)-3-hydroxy-1-nonenyl]-7-hydroxybicyclo[3.3.0]octane, (003) (1S,5R,6R,7R)-3-methylene-6-[(E,3S,5S)-3-hydroxy-5-methyl-1-nonenyl]-7-hydroxybicyclo[3.3.0O]octane, (004) (1S,5R,6R,7R)-3-methylene-6-[(E,3S,5R)-3-hydroxy-5-methyl-1-nonenyl]-7-hydroxybicyclo[3.3.0O]octane, (005) (1S,5R,6R,7R)-3-methylene-6-[(E,3S)-3-hydroxy-9-methyl-1,8-decanedienyl-7-hydroxybicyclo[3.3.0]octane, (006) (1S,5R,6R,7R)-3-methylene-6-[(E,3S)-3-hydroxy-4-methyloct-2-en-6-yl]-7-hydroxybicyclo[3.3.0]octane, (007) (1S,5R,6R,7R)-3-methylene-6-[(E,3S)-3-hydroxy-3-cyclopentyl-1-propenyl]-7-hydroxybicyclo[3.3.0]octane, (008) (1S,5R,6R,7R)-3-methylene-6-[(E,3S)-3-hydroxy-3-cyclohexyl-1-propenyl]-7-hydroxybicyclo[3.3.0]octane, (009) (1S,5R,6R,7R)-3-methylene-6-[(E,3S)-3-hydroxy-3-methyl-1-octenyl]-7-hydroxybicyclo[3.3.0]octane, (010) (1S,5R,6R,7R)-3-methylene-6-[(E,3S)-3-hydroxy-3-vinyl-1-octenyl]-7-hydroxybicyclo[3.3.0]octane, (011) (1S,5R,6R,7R)-3-methylene-6-[(E)-4-hydroxy-1-octenyl]-7-hydroxybicyclo[3.3.0]octane, (012) (1S,5R,6R,7R)-3-methylene-6-[(E,4S)-4-hydroxy-1-octenyl]-7-hydroxybicyclo[3.3.0]octane.

(013) (1S,5R,6R,7R)-3-methylene-6-[(E)-4-hydroxy-4-methyl-1-octenyl-7-hydroxybicyclo[3.3.0]octane, (014) (1S,5R,6R,7R)-3-methylene-6-[(E,4S)-hydroxy-4-methyl-1-octenyl-7-hydroxybicyclo[3.3.0]octane, (015) (1S,5R,6R,7R)-3-methylene-6-[(E)-4-hydroxy-4-methyl-1-nonenyl]-7-hydroxybicyclo[3.3.0]octane, (016) (1S,5R,6R,7R)-3-methylene-6-[(E)-4-hydroxy-4-vinyl-1-octenyl]-7-hydroxybicyclo[3.3.0]octane.

In the process of the present invention, a free hydroxy group is supplied to the reaction in a protected form. When a t-butyldimethylsilyl group is used as a typical protective group, specific examples of the 2,6,7-trisubstituted-3-methylenebicyclo[3.3.0]octanes of the above formula (2) as starting materials in the process of the present invention are as follows.

(101) Bis(t-butyldimethylsilyl)ethers of the compounds (001) to (016) in the 2-position of which a diethoxyphosphoryloxy group is substituted, (102) Bis(t-butyldimethylsilyl)ethers of the compounds (001) to (016) in the 2-position of which a dipropoxyphosphoryloxy group is substituted, (103) Bis(t-butyldimethylsilyl)ethers of the compounds (001) to (016) in the 2-position of which a diphenoxyphosphoryloxy group is substituted, (104) Bis(t-butyldimethylsilyl)ethers of the compounds (001) to (016) in the 2-position of which a dimethoxythiophosphoryloxy group is substituted, (105) Bis(t-butyldimethylsilyl)ethers of the compounds (001) to (016) in the 2-position of which a diethoxythiophosphoryloxy group is substituted, (106) Bis(t-butyldimethylsilyl)ethers of the compounds (001) to (016) in the 2-position of which a dimethoxyphosphorylthio group is substituted, (107) Bis(t-butyldimethylsilyl)ethers of the compounds (001) to (016) In the 2-position of which a diethoxyphosphorylthio group is substituted, (108) Bis(t-butyldimethylsilyl)ethers of the compounds (001) to (016) in the 2-position of which a methoxycarbonyloxy group is substituted, (109) Bis(t-butyldimethylsilyl)ethers of the compounds (001) to (016) in the 2-position of which a ethoxycarbonyloxy group is substituted, (110) Bis(t-butyldimethylsilyl)ethers of the compounds (001) to (016) in the 2-position of which a propyloxycarbonyloxy group is substituted, (111) Bis(t-butyldimethylsilyl)ethers of the compounds (001) to (016) in the 2-position of which an allyloxycarbonyloxy group is substituted, (112) Bis(t-butyldimethylsilyl)ethers of the compounds (001) to (016) in the 2-position of which a butyloxycarbonyloxy group is substituted, (113) Bis(t-butyldimethylsilyl)ethers of the compounds (001) to (016) In the 2-position of which a hexyloxycarbonyloxy group is substituted, (114) Bis(t-butyldimethylsilyl)ethers of the compounds (001) to (016) in the 2-position of which a phenoxycarbonyloxy group is substituted, (115) Compounds of (101) to (114) of which the bis(t-butyldimethylsilyl)ether is replaced with bis(t-butyldiphenylsilyl)ether, (116) Compounds of (101) to (114) of which the bis(t-butyldimethylsilyl)ether is replaced with (2-tetrahydropyranyl)ether, (117) Compounds of (101) to (114) of which the bis(t-butyldimethylsilyl)ether is replaced with bis(2-ethoxyethoxy)ether, and (118) Compounds of (101) to (114) of which the bis(t-butyldimethylsilyl)ether is replaced with bis(acetoxy)ether are included, while they are not limited to these.

In the process of the present invention, the above 2,6,7-trisubstituted-3methylenebicyclo[3.3.0]octanes of the above formula (2) are allowed to react with the organic zinc compound of the above formula (3) in the presence of cuprous salts of the formula (4).

In the above formula (3), m is an integer of 0 to 4, and $R^3$ is $C_1$–$C_{10}$ alkyl, phenyl, benzyl or naphthyl group. $X^1$ is a halogen atom. The halogen atom includes a fluorine atom, a chlorine atom, a bromine atom and iodine atom. W is phenylene, $C_3$–$C_7$ cycloalkylene group or thiphendiyl group. The alkyl group as $R^3$ may be linear or branched. Examples of the $C_1$–$C_{10}$ alkyl group and the $C_3$–$C_7$ cycloalkyl group are apparent per se.

The organic zinc compound of the above formula (3) is prepared from corresponding halides and metal zinc according to the method of P. Knochel, et al [Tetrahedron Letters, 31, 4413 (1990)], or from halogenated benzyl derivatives and metal zinc according to the method of P. Knochel, et al [Journal of Organic Chemistry, 53, 5789 (1988)]. That is, in an organic solvent such as tetrahydrofuran or dimethylformamide, metal zinc is activated with 1,2-dibromoethane and then with trimethylchlorosilane, then, corresponding halides are added in an amount equivalent to that of the metal zinc, and they are allowed to react at −78° C. to 50° C. for several hours to several days, whereby a solution of the intended organic zinc compound is prepared.

Typical and specific examples of the organic zinc compound of the above formula (3) in the form of halides as its precursor include methyl p-fluorobenzoate, methyl p-chlorobenzoate, methyl p-bromobenzoate, methyl p-iodobenzoate, methyl p-fluoromethylbenzoate, methyl p-chloromethylbenzoate, methyl p-bromomethylbenzoate, methyl p-iodomethylbenzoate, methyl p-fluoroethylbenzoate, methyl p-chloroethylbenzoate, methyl p-bromoethylbenzoate, methyl p-iodoethylbenzoate, methyl p-fluoropropylbenzoate, methyl p-chloropropylbenzoate, methyl p-bromopropylbenzoate, methyl p-iodopropylbenzoate, methyl p-fluorobutylbenzoate, methyl p-chlorobutylbenzoate, methyl p-bromobutylbenzoate, methyl p-iodobutylbenzoate, and ethyl esters, propyl esters, isopropyl esters, butyl esters, isobutyl esters, t-butyl esters, phenyl esters, benzyl esters and naphthyl esters of these p-substituted benzoic acids, and further, m-substituted and o-substituted compounds of these. Of these compounds, bromine derivatives and iodine derivatives are preferred. It is sufficient if an organic zinc compound represented by the above formula (3) can be prepared by the reaction of the halides with metal zinc, and there is no special limitation to be imposed on the above compounds.

In the cuprous salts of the above formula (4), $X^2$ is a cyano group or a halogen atom. The halogen atom includes a chlorine atom, a bromine atom and an iodine atom, and any one of these can be preferably used.

In the process of the present invention, preferably, the cuprous salts of the above formula (4) and a solution of the organic zinc compound of the above formula (3) are first brought into contact with each other to form an organic copper zinc complex. This preparation method is also carried out according to the above method of P. Knochel et al. That is, the organic copper zinc complex is formed by reacting the organic zinc compound with the cuprous salts in an equivalent amount in the presence of an organic medium such as tetrahydrofuran or dimethylformamide at a temperature between −30° C. and 40° C. for several minutes to several hours. The co-presence of a lithium salt such as lithium chloride enhances the effect on the complex formation and brings favorable results in many cases. The amount of this lithium salt per mole of the cuprous salt is 1 to 5 mol, particularly preferably 2 to 3 mol.

Preferably, the process of the present invention is carried out by reacting the so-prepared organic copper zinc complex with the 2,6,7-trisubstituted-3-methylenebicyclo[3.3.0]octanes of the above formula (2). Examples of the organic medium used in the reaction include ether-based media such as diethyl ether, tetrahydrofuran, dioxane and 1,2-dimethoxyethane; and nitrogen-containing media such as dimethylformamide, dimethylacetamide and N-methyl-2-pyrrolidone (NMP).

Further, as will be described later, the solvent system from the preparation of the 2,6,7-trisubstituted-3-methylenebicyclo[3.3.0]octanes of the above formula (2) may be used as it is. The amount of the above organic medium is an amount sufficient for smoothly proceeding with the intended reaction smoothly, and generally, the reaction is carried out in the presence of the organic medium in an amount ranging from 1 to 1,000 ml, preferably 10 to 100 ml, in terms of a reaction scale represented by mmol. In the stoichiometry, the organic copper zinc complex undergoes an equimolar reaction with the 2,6,7-trisubstituted-3-methylenebicyclo[3.3.0]octanes of the above formula (2), but the organic copper zinc complex may be used in an excess amount. The molar amount of the organic copper zinc complex is generally 1 to 30 times, preferably 1 to 15 times.

The temperature for the reaction between the organic copper complex and the 2,6,7-trisubstituted-3-methylenebicyclo[3.3.0]octanes of the above formula (2) is in the range of −90° C. to 100°, preferably in the range of −78° C. to 50° C. The reaction time varies depending upon the cuprous salts used starting materials or reaction temperature. The reaction is generally carried out, while tracing the disappearance of the starting materials with an analysis means such as thin layer chromatography, and the reaction terminates after several minutes to several tens hours. In the isolation of the interphenylene type isocarbacyclins which are reaction products after termination of the reaction, they are separated and purified by ordinary post-treatment means such as extraction, washing, drying, concentration, subsequent chromatography, and distillation.

According to the above reaction, there are formed interphenylene type isocarbacyclins of the following formula (1) in two sites of which the hydroxyl groups are protected.

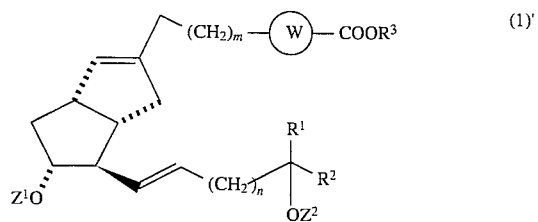

wherein

W, $R^1$, $R^2$, $R^3$, $Z^1$, $Z^2$, m and n are as defined before.

In the process of the present invention, there may be optionally carried out a deprotection reaction to bring the protected hydroxy groups to free hydroxyl group in a final form for a drug and a reaction for the hydrolysis of, or the salt-forming from, the substituent $COOR^3$ of the phenyl group.

The deprotection reaction is known per se. When the protective group is a group which forms a acetal bond together with an oxygen atom to which it bonds. The deprotection reaction is preferably carried out, for example, in the presence of a catalyst such as acetic acid, p-toluenesulfonic acid, pyridinium p-toluenesulfonate or a cation-exchange resin and in the presence of water, methanol, ethanol or a reaction solvent such as tetrahydrofuran ethyl ether, dioxane, acetone or acetonitrile in the co-presence of water, methanol or ethanol. The reaction is generally carried out at a temperature ranging from −78° C. to +50° C. for approximately 10 minutes to 3 days. When the protective group is a tri($C_1$–$C_7$ hydrocarbon)silyl group, the reaction is preferably carried out in the above reaction solvent at a temperature similar to the above in the presence of a catalyst selected from acids such as acetic acid, p-toluenesulfonic acid and pyridinium p-toluenesulfonate, or it is preferably carried out at a temperature similar to the above for as long a period of time as the above in the presence of a fluorine-containing reagent such as tetrabutylammonium fluoride, cesium fluoride, hydrofluoric acid or hydrogen fluoride-pyridine in the presence of a reaction solvent such as tetrahydrofuran, ethyl ether, dioxane, acetone or acetonitrile. When each protective group forms an ester bond together with the oxygen atom to which it bonds, the reaction may be carried out by the hydrolysis in an aqueous solution of lithium hydroxide, sodium hydroxide, potassium hydroxide or calcium hydroxide, water-alcohol mixed solvents, or a methanol or ethanol solution containing sodium methoxide, potassium methoxide or sodium ethoxide.

As described above, according to the present invention, the α-chain-modified isocarbacyclins of the formula (1), i.e., interphenylene type isocarbacyclins can be produced.

Those of the above formula (1) in which W is a phenylene group are preferred, and those of the above formula (1) in which $R^{30}$ is a hydrogen atom, a $C_1$–$C_4$ alkyl group or one equivalent amount of a cation and each of $Z^{10}$ and $Z^{20}$ is a hydrogen atom are another preferred embodiments.

The α-chain-modified isocarbacyclins of the above formula (1) can be obtained as the intended interphenylene type isocarbacyclin derivatives of the above formula (1) by preparing alcohol derivatives [corresponding to a compound of the above formula (2) in which Y is a hydroxyl group] as the starting material, adding the above organic copper zinc complex to the reaction system in which the alcohol derivatives have been prepared, and carrying out the reaction.

Specific examples of the α-chain-modified isocarbacyclins of the above formula (1) include compounds formed from any combinations of compounds described as the 2,6,7-trisubstituted-3-methylenebicyclo[3.3.0]octanes of the above formula (2) with the organic zinc compound of the above formula (3). Examples of the compounds of the formula (1) in which all of $Z^{10}$ $Z^{20}$ and $R^{30}$ are hydrogen atoms as typical examples are as follows.

(01) (1S,5S,6S,7R)-3-(o-carboxybenzyl)-6-[(1E,3S)-3-hydroxy-1-octenyl]-7-hydroxybicyclo[3.3.0]-2-octene,

(02) (1S,5S,6S,7R)-3-(m-carboxybenzyl)-6-[(1E,3S)-3-hydroxy-1-octenyl]-7-hydroxybicyclo[3.3.0]-2-octene,

(03) (1S,5S,6S,7R)-3-(p-carboxybenzyl)-6-[(1E,3S)-3-hydroxy-1-octenyl]-7-hydroxybicyclo[3.3.0]-2-octene,

(04) (1S,5S,6S,7R)-3-(o-carboxybenzyl)-6-[(1E,3S)-3-hydroxy-4-methyl-1-octenyl]-7-hydroxybicyclo[3.3.0]-2-octene,

(05) (1S,5S,6S,7R)-3-(o-carboxybenzyl)-6-[(1E,3S)-3-hydroxy-4,4-dimethyl-1-octenyl]-7-hydroxybicyclo[3.3.0]-2-octene,

(06) (1S,5S,6S,7R)-3-(o-carboxybenzyl)-6-[(1E,3S)-3-hydroxy-5-methyl-1-octenyl]-7-hydroxybicyclo[3.3.0]-2-octene,

(07) (1S,5S,6S,7R)-3-(o-carboxybenzyl)-6-[(1E,3S)-3-hydroxy-5-methyl-1-nonenyl]-7-hydroxybicyclo[3.3.0]-2-octene,

(08) (1S,5S,6S,7R)-3-(o-carboxybenzyl)-6-[(1E,3S)-3-hydroxy-3-cyclopentyl-1-propenyl]-7-hydroxybicyclo[3.3.0]-2-octene,

(09) (1S,5S,6S,7R)-3-(o-carboxybenzyl)-6-[(1E,3S)-3-hydroxy-3-cyclohexyl]-7-hydroxybicyclo[3.3.0]-2-octene,

(10) (1S,5S,6S,7R)-3-(o-carboxybenzyl)-6-[(1E,4S)-4-hydroxy-4-methyl-1-octenyl]-7-hydroxybicyclo[3.3.0]-2-octene,

(11) (1S,5S,6S,7R)-3-(o-carboxybenzyl)-6-[(1E,4R)-4-hydroxy-4-methyl-1-octenyl]-7-hydroxybicyclo[3.3.0]-2-octene,

(12) (1S,5S,6S,7R)-3-(o-carboxybenzyl)-6-[(1E)-4-hydroxy-4-vinyl-1-octenyl]-7-hydroxybicylco3.3.0]-2-octene, (13)–(21) 3-(m-carboxybenzyl) derivatives of (04) to (12), (22)–(30) 3-(p-carboxybenzyl) derivatives of (04) to (12),

(31) (1S,5S,6S,7R)-3-[2-(o-carboxyphenyl)ethyl]-6-[(1E,3S)-3-hydroxy-1-octenyl]-7-hydroxybicyclo[3.3.0]-2-octene,

(32) (1S,5S,6S,7R)-3-[2-(o-carboxyphenyl)ethyl]-6-[(1E,3S)-3-hydroxy-4-methyl-1-octenyl]-7-hydroxybicyclo[3.3.0]-2-octene,

(33) (1S,5S,6S,7R)-3-[2-(o-carboxyphenyl)ethyl]-6-[(1E,3S)-3-hydroxy-4,4-dimethyl-1-octenyl]-7-hydroxybicyclo[3.3.0]-2-octene,

(34) (1S,5S,6S,7R)-3-[2-(o-carboxyphenyl)ethyl]-6-[(1E,3S)-3-hydroxy-5-methyl-1-octenyl]-7-hydroxybicyclo[3.3.0]-2-octene,

(35) (1S,5S,6S,7R)-3-[2-(o-carboxyphenyl)ethyl]-6-[(1E,3S)-3-hydroxy-5-methyl-1-nonenyl]-7-hydroxybicyclo[3.3.0]-2-octene,

(36) (1S,5S,6S,7R)-3-[2-(o-carboxyphenyl)ethyl]-6-[(1E,3S)-3-hydroxy-3-cyclopentyl-1-propenyl]-7-hydroxybicyclo[3.3.0]-2-octene,

(37) (1S,5S,6S,7R)-3-[2-(o-carboxyphenyl)ethyl]-6-[(1E,3S)-3-hydroxy-3-cyclohexyl]-7-hydroxybicyclo[3.3.0]-2-octene,

(38) (1S,5S,6S,7 g)-3-[2-(o-carboxyphenyl)ethyl]-6-[(1E,4S)-4-hydroxy-4-methyl-1-octenyl]-7-hydroxybicyclo[3.3.0]-2-octene,

(39) (1S,5R,6S,7R)-3-[2-(o-carboxyphenyl)ethyl]-6-[(1E,4S)-4-hydroxy-4-methyl-1-octenyl]-7-hydroxybicyclo[3.3.0]-2-octene,

(40) (1S,5S,6S,7R)-3-[2-(o-carboxyphenyl)ethyl]-6-[(1E)-4-hydroxy-4-vinyl-1-octenyl]-7-hydroxybicyclo[3.3.0]-2-octene, (41)–(50) 3-[2-(m-carboxyphenyl)ethyl] derivatives of (31) to (40).

(51)–(60) 3-[2-(p-carboxyphenyl)ethyl] derivatives of (31) to (40),

(61) (1S,5S,6S,7R)-3-[3-(o-carboxyphenyl)propyl]-6-[(1E,3S)-3-hydroxy-1-octenyl]-7-hydroxybicyclo[3.3.0]-2-octene,

(62) 3-[3-(o-carboxyphenyl)propyl] derivative of (61),

(63) 3-[3-(m-carboxyphenyl)propyl] derivative of (61),

(64) (1S,5S,6S,7R)-3-[3-(o-carboxyphenyl)propyl]-6-[(1E,3S)-3-hydroxy-4-methyl-1-octenyl]-7-hydroxybicyclo[3.3.0]-2-octene,

(65) (1S,5S,6S,7R)-3-[3-(o-carboxyphenyl)propyl]-6-[(1E,3S)-3-hydroxy-4,4-dimethyl-1-octenyl]-7-hydroxybicyclo[3.3.0]-2-octene,

(66) (1S,5S,6S,7R)-3-[3-(o-carboxyphenyl)propyl]-6-[(1E,3S)-3-hydroxy-5-methyl-1-octenyl]-7-hydroxybicyclo[3.3.0]-2-octene,

(67) (1S,5S,6S,7R)-3-[3-(o-carboxyphenyl)propyl]-6-[(1E,3S)-3-hydroxy-5-methyl-1-nonenyl]-7-hydroxybicyclo[3.3.0]-2-octene,

(68) (1S,5S,6S,7R)-3-[3-(o-carboxyphenyl)propyl]-6-[(1E,3S)-3-hydroxy-3-cyclopentyl-1-propenyl]-7-hydroxybicyclo[3.3.0]-2-octene.

(69) (1S,5S,6S,7R)-3-[3-(o-carboxyphenyl)propyl]-6-[(1E,3S)-3-hydroxy-3-cyclohexyl]-7-hydroxybicyclo[3.3.0]-2-octene,

(70) (1S,5S,6S,7R)-3-[3-(o-carboxyphenyl)propyl]-6-[(1E,4S)-4-hydroxy-4-methyl-1-octenyl]-7-hydroxybicyclo[3.3.0]-2-octene,

(71) (1S,5S,6S,7R)-3-[3-(o-carboxyphenyl)propyl]-6-[(1S,4R)-4-hydroxy-4-methyl-1-octenyl]-7-hydroxybicyclo[3.3.0]-2-octene,

(72) (1R,5S,6S,7S)-3-[3-(o-carboxyphenyl)propyl]-6-[(1E)-4-hydroxy-4-vinyl-1-octenyl]-7-hydroxybicyclo[3.3.0]-2-octene, (73)–(81) 3-[3-(m-carboxyphenyl)propyl] derivatives of (64) to (72), (82)–(90) 3-[3-(p-carboxyphenyl)propyl] derivatives of (64) to (72),

(91) (1S,5S,6S,7R)-3-[4-(o-carboxyphenyl)butyl]-6-[(1E,3S)-3-hydroxy-1-octenyl]-7-hydroxybicyclo[3.3.0]-2-octene,

(92) (1S,5S,6S,7R)-3-[4-(o-carboxyphenyl)butyl]-6-[(1E,3S)-3-hydroxy-4-methyl-1-octenyl]-7-hydroxybicyclo[3.3.0]-2-octene,

(93) (1S,5S,6S,7R)-3-[4-(o-carboxyphenyl)butyl]-6-[(1E,3S)-3-hydroxy-4,4-dimethyl-1-octenyl]-7-hydroxybicyclo[3.3.0]-2-octene,

(94) (1S,5S,6S,7R)-3-[4-(o-carboxyphenyl)butyl]-6-[(1E,3S)-3-hydroxy-5-methyl-1-octenyl]-7-hydroxybicyclo[3.3.0]-2-octene,

(95) (1S,5S,6S,7R)-3-[4-(o-carboxyphenyl)butyl]-6-[(1E,3S)-3-hydroxy-5-methyl-1-nonenyl]-7-hydroxybicyclo[3.3.0]-2-octene,

(96) (1S,5S,6S,7R)-3-[4-(o-carboxyphenyl)butyl]-6-[(1E,3S)-3-hydroxy-3-cyclopentyl-1-propenyl]-7-hydroxybicyclo[3.3.0]-2-octene,

(97) (1S,5S,6S,7R)-3-[4-(o-carboxyphenyl)butyl]-6-[(1E,3S)-3-hydroxy-3-cyclohexyl]-7-hydroxybicyclo[3.3.0]-2-octene,

(98) (1S,5S,6S,7R)-3-[4-(o-carboxyphenyl)butyl]-6-[(1E,4S)-4-hydroxy-4-methyl-1-octenyl]-7-hydroxybicyclo[3.3.0]-2-octene,

(99) (1S,5S,6S,7R)-3-[4-(o-carboxyphenyl)butyl]-6-[(1E,4S)-4-hydroxy-4-methyl-1-octenyl]-7-hydroxybicyclo[3.3.0]-2-octene, (100) (1S,5S,6S,7R)-3-[4-(o-carboxyphenyl)butyl]-6-[(1E)-4-hydroxy-4-vinyl-1-octenyl]-7-hydroxybicyclo[3.3.0]-2-octene, (101)–(110) 3-[4-(m-carboxyphenyl)butyl] derivatives of (91) to (100), (111)–(120) 3-[4-(p-carboxyphenyl)butyl] derivatives of (91) to (100), (121) (1S,5S,6S,7R)-3-[5-(o-carboxyphenyl)pentyl]-6-[(1E,3S)-3-hydroxy-1-octenyl]-7-hydroxybicyclo[3.3.0]-2-octene, (122) (1S,5S,6S,7R)-3-[5-(o-carboxyphenyl)pentyl]-6-[(1E,3S)-3-hydroxy-4-methyl-1-octenyl]-7-hydroxybicyclo[3.3.0]-2-octene, (123) (1S,5S,6S,7R)-3-[5-(o-carboxyphenyl)pentyl]-6-[(1E,3S)-3-hydroxy-4,4-dimethyl-1-octenyl]-7-hydroxybicyclo[3.3.0]-2-octene, (124) (1S,5S,6S,7R)-3-[5-(o-carboxyphenyl)pentyl]-6-[(1E,3S)-3-hydroxy-5-methyl-1-octenyl]-7-hydroxybicyclo[3.3.0]-2-octene, (125) (1S,5S,6S,7R)-3-[5-(o-carboxyphenyl)pentyl]-6-[(1E,3S)-3-hydroxy-5-methyl-1-nonenyl]-7-hydroxybicyclo[3.3.0]-2-octene, (126) (1S,5S,6S,7R)-3-[5-(o-carboxyphenyl)pentyl]-6-[(1E,3S)-3-hydroxy-3-cyclopentyl-1-propenyl]-7-hydroxybicyclo[3.3.0]-2-octene, (127) (1S,5S,6S,7R)-3-[5-(o-carboxyphenyl)pentyl]-6-[(1E,3S)-3-hydroxy-3-cyclohexyl]-7-hydroxybicyclo[3.3.0]-2-octene, (128) (1S,5S,6S,7R)-3-[5-(o-carboxyphenyl)pentyl]-6-[(1E,4S)-4-hydroxy-4-methyl-1-octenyl]-7-hydroxybicyclo[3.3.0]-2-octene, (129) (1S,5S,6S,7R)-3-[5-(o-carboxyphenyl)pentyl]-6-[(1E,4S)-4-hydroxy-4-methyl-1-octenyl]-7-hydroxybicyclo[3.3.0]-2-octene, (130) (1S,5S,6S,7R)-3-[5-(o-carboxyphenyl)pentyl]-6-[(1)-4-hydroxy-4-vinyl-1-octenyl]-7-hydroxybicyclo[3.3.0]-2-octene, (131)–(140) 3-[5-(m-carboxyphenyl)pentyl] derivatives of (121) to (130), (141)–(150) 3-[5-(p-carboxyphenyl)pentyl] derivatives of (121) to (130).

As described above, the process for the production of α-chain-modified isocarbacyclins, provided by the present invention, has the following characteristic features. That is, the characteristic features are that (1) The starting materials, 2,6,7-trisubstituted-3-methylenebicyclo[3.3.0]octanes of the formula (2), are stabler than corresponding tosylates and halides.

(2) All steric isomers of the 2-position of the starting materials have high positional selectivity and give intended products of the formula (1).

(3) Similar reactions are carried out not only with a salt of cuprous cyanide, but also with a halogenated cuprous salt.

(4) An organic zinc compound and an organic copper zinc complex are characteristically inert to an ester functional group, and the reaction therefore can be carried out without protecting the ester group. The production process of the present invention can be therefore said to be effective in view of high selectivity, high yields and shortened steps and to be excellent in industry.

Further, the α-chain-modified isocarbacyclins of this invention are useful as drugs for inhibiting the hypertrophy and occlusion of a blood vessel caused mainly by the proliferation of blood vessel smooth muscle cells after various angioplastic operations, arterial bypass operations and organic transplantations, as drugs for the prevention and therapy of blood vessel hypertrophy and occlusion (or a drug for the inhibition of the proliferation of blood vessel smooth muscle cells) and further as drugs for the prevention and therapy of arterial sclerosis.

EXAMPLES

The present invention will be explained further in detail hereinafter with reference to Examples. In the formulae in Examples, $OZ^1$ stands for a t-butyldimethylsilyloxy group, OZ² stands for a trimethylsilyloxy group, and OZ³ stands for a t-butyldiphenylsilyloxy group.

Example 1

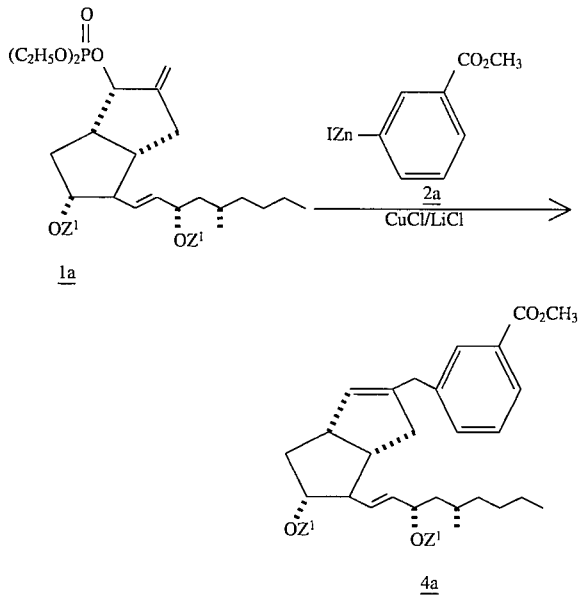

Zinc (0.850 g, 13 mmol) was placed in a 30-ml reactor, and after the reactor was flushed with argon gas, distilled tetrahydrofuran (2 ml) was added. Added thereto was 80 μl of 1,2-dibromoethane, and the mixture was stirred under heat at 65° C. for 1 minute and then stirred at room temperature for 30 minutes. Then, 100 μl of trimethylchlorosilane was added, and the mixture was stirred at room temperature for 30 minutes. Thereafter, a solution of methyl-3-iodobenzoate (2.62 g, 10 mmol) in dry dimethylformamide (10 ml) was added, and the mixture was stirred at 40° C. for 16 hours. A solution of cuprous chloride (0.990 g, 10 mmol) and lithium chloride (0.848 g, 20 mmol) in distilled tetrahydrofuran (10 ml) was prepared in a 50-ml reactor, and the above liquid mixture was added thereto at room temperature. The mixture was stirred at 30° C. for 1 hour. Added to this liquid mixture was a solution of (1S,5R,6R,7R)-2-diethoxyphosphoryloxy-3-methylene-6-[(1E,3S,5S)-3-t-butyldimethylsilyloxy-5-methyl-1-nonenyl]-7-t-butyldimethyl-silyloxybicyclo[3.3.0]octane 1a (0.672 g, 1 mmol) in dry tetrahydrofuran (10 ml) at room temperature, and the mixture was stirred at 30° C. for 2 hours. Added to the liquid mixture was 200 ml of a saturated ammonium chloride aqueous solution to terminate the reaction, and the reaction mixture was extracted with ethyl acetate (200 ml×2 times). A separated organic layer was washed with an aqueous sodium chloride solution, dried over anhydrous magnesium sulfate and concentrated to give a crude product (1.97 g). This product was subjected to silica gel chromatography (silica gel 40 g; elution liquid hexane:ethyl acetate=20:1) to give an intended compound 4a (0.641 g, 0.98 mmol, 98%).

$^1$H-NMR (CDCl$_3$, ppm) δ; 7.85(2H,m), 7.35(2H,m), 5.45(2H,m), 5.30(1H,d,J=1.2 Hz), 4.10(1H,m), 3.90(3H,s), 3.70(1H,m), 3.40(2H,bs), 3.00(1H,m), 2.40–2.20(3H,m), 1.95–1.80(2H,m), 1.40–1.10(10H,m), 0.90–0.80(18H,m), 0.09(18 h,s).

IR (liquid film) cm$^{-1}$: 2955, 2920, 1725, 1607, 1590, 965, 735.

Example 2

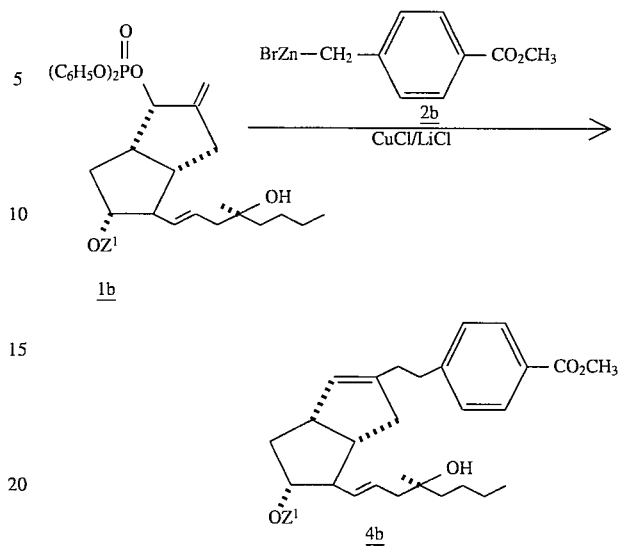

Zinc (0.850 g, 13 mmol) was placed in a 50-ml reactor, and after the reactor was flushed with argon gas, distilled tetrahydrofuran (2 ml) was added. Added thereto was 80 μl of 1,2-dibromoethane, and the mixture was stirred under heat at 65° C. for 1 minute and then stirred at room temperature for 30 minutes. Then, 100 μl of trimethylchlorosilane was added, and the mixture was stirred at room temperature for 30 minutes. Thereafter, a solution of methyl-4-bromomethylbenzoate (2.290 g, 10 mmol) in distilled tetrahydrofuran (15 ml) was added at 0° C., and the mixture was stirred at 0° C. for 3 hours and then cooled to −78° C. A solution of cuprous chloride (0.990 g, 10 mmol) and lithium chloride (0.848 g, 20 mmol) in distilled tetrahydrofuran (10 ml) was prepared in a 100-ml reactor and cooled to −78° C., and the above liquid mixture was added thereto at −78° C. The mixture was temperature-elevated to −20° C., stirred for 30 minutes and then re-cooled to −78° C. Added to this liquid mixture was a solution of (1S,5R,6R,7R)-2-diphenoxyphosphoryloxy-3-methylene-6-[(1E,4R)4-methyl-4-hydroxy-1-octenyl]-7-t-butyldimethylsilyloxybicyclo[3.3.0]octane 1b (0.640 g, 1 mmol) in dry tetrahydrofuran (10 ml) at −78° C., and the mixture was stirred at −78° C. for 2 hours. Added to the liquid mixture was 200 ml of a saturated ammonium chloride aqueous solution to terminate the reaction, and the reaction mixture was extracted with ethyl acetate (200 ml×2 times). A separated organic layer was washed with an aqueous sodium chloride solution, dried over anhydrous magnesium sulfate and concentrated to give a crude product (2.10 g). This product was subjected to silica gel chromatography (silica gel 40 g; elution liquid hexane:ethyl acetate=20:1–10:1) to give an intended compound 4b (0.496 g, 088 mmol, 88%).

$^1$H-NMR (CDCl$_3$, ppm) δ; 7.95 (2H,d,J=7.5 Hz), 7.20(2H,d,J=7.5 Hz)m), 5.45(2H,m), 5.25(1H,d,J=1.2 Hz), 3.90(3H,s), 3.70(1H,m), 3.00(1H,m), 2.80(2H,t,J=7.5 Hz), 2.40–1.90(8H,m), 1.60–1.10(9H,m), 1.15(3H,s), 1.95–1.80(9H,m), 0.09(9H,s).

IR (liquid film) cm$^{-1}$: 3340, 2956, 2930, 2915, 1682, 1611, 965, 735.

Examples 3–4

Reactions of reactants 1b and 1c (1 mmol) with a zinc compound (10 mmol) prepared from methyl-3-iodobenzoate (10 mmol) were carried out in the presence of CuCl (10 mmol) and LiCl (20 mmol) in the same manner as in Example 1. The reaction mixtures were post-treated and column-separated to give corresponding products 4c and 4 d at yields shown in Table 1. The NMR spectra of the products shown in Table 2 show that all the products were almost intended positional isomers and the reactions proceeded with highly positional selectivity.

4c: IR (liquid film) cm$^{-1}$: 3340, 2956, 2932, 1715, 1607, 965, 735

4 d IR (liquid film) cm$^{-1}$: 2956, 2932, 1715, 1607, 965, 735

Examples 5–6

Reactions of reactants 1a and 1c with a zinc compound (10 mmol) prepared from methyl-4-(bromomethyl)benzoate (10 mmol) were carried out in the presence of CuCl (10 mmol) and LiCl (20 mmol) in the same manner as in Example 2. The reaction mixtures were post-treated and column-separated to give corresponding products 4e and 4 f at yields shown in Table 3. Table 4 shows the analysis results thereof.

TABLE 1

| Example | Reactant | Product | Yield (%) |
|---|---|---|---|
| 3 | 1b | 4c | 92 |
| 4 | 1c | 4d | 96 |

TABLE 2

| Example | Product | $^1$H-NMR (CDCl$_3$, ppm) δ |
|---|---|---|
| 3 | 4c | 7.85(2H, m), 7.38(2H, m), 5.45(2H, m) 5.35(1H, d, J=1.2Hz), 3.90(3H, s), 3.78(1H, m), 3.40(2H, s), 3.00(1H, m), 2.40–1.85(8H, m), 1.60(1H, s), 1.50–1.20(6H, m), 1.15(3H, s), 1.00–0.80(12H, m), 0.10–0.00(6H, m) |
| 4 | 4d | 7.85(2H, m), 7.38(2H, m), 5.40(2H, m), 5.30(1H, d, J=1.2Hz), 4.10(1H, m), 3.85(3H, s), 3.75(1H, m), 3.30(2H, s) 2.95(1H, m), 2.40–2.20(3H, m), 1.95–1.80(2H, m), 1.65–1.20(9H, m) 0.95–0.85(21H, m), 0.10–0.00(12H, m) |

TABLE 3

| Example | Reactant | Product | Yield (%) |
|---|---|---|---|
| 5 | 1a | 4e | 88 |
| 6 | 1c | 4f | 92 |

TABLE 4

| Example | Product | $^1$H-NMR (CDCl$_3$, ppm) δ |
|---|---|---|
| 5 | 4e | 7.95(2H, d, J = 7.5Hz), 7.25(2H, d, J = 7.5Hz), 5.50(2H, m), 5.25(1H, d, J=1.2Hz), 4.15(1H, m), 3.85(3H, s), 3.85(1H, m), 3.00(1H, m), 2.80(2H, t, J=8Hz), 2.40–1.80(7H, m), 1.40–1.20(10H, m) 0.90–0.85(24H, m), 0.10–0.00(12H, m) |
| 6 | 4f | 7.95(2H, d, J=7.5Hz), 7.25(2H, d, J=7.5Hz), 5.50(2H, m), 5.25(1H, d, J=1.2Hz), 4.15(1H, m), 3.85(3H, s), 3.85(1H, m), 3.00(1H, m), 2.80(2H, t, J=8Hz), 2.40–1.80(7H, m), 1.40–1.20(9H, m), 0.90–0.85(21H, m), 0.10–0.00(12H, m) |

4e: IR (liquid film) cm$^{-1}$: 2955, 2920, 1724, 1607, 1590, 965, 735

4 f: IR (liquid film) cm$^{-1}$: 2955, 2920, 1724, 1607, 1590, 965, 735

-continued

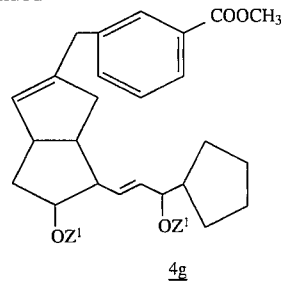

4g

A reaction of a reactant 1(1 mmol) with a zinc compound (10 mmol) prepared from methyl-3-iodobenzoate (10 mmol) was carried out in the presence of CuCl (10 mmol) and LiCl (20 mmol) in the same manner as in Example 1. The reaction mixture was post-treated and column-separated to give a corresponding product 4 g (yield: 86%).

Example 7

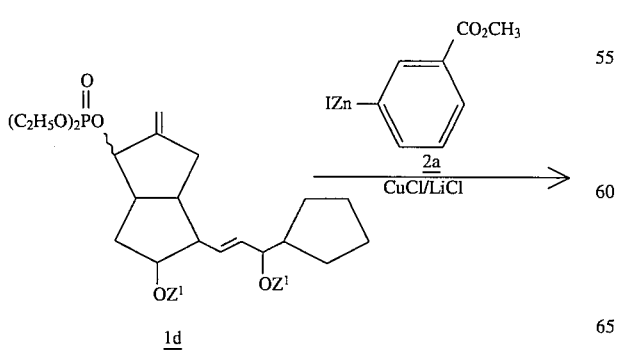

Example 8

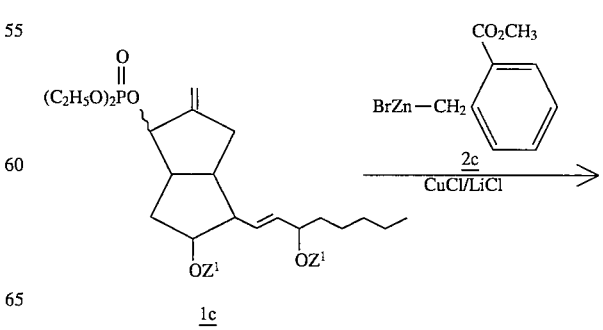

-continued

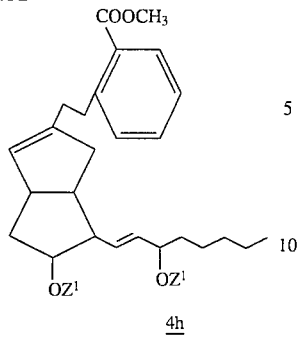

4h

A reaction of a reactant 1c (1 mmol) with a zinc compound (10 mmol) prepared from methyl-2-(bromomethyl)benzoate (10 mmol) was carried out in the presence of CuCl (10 mmol) and LiCl (20 mmol) in the same manner as in Example 2. The reaction mixture was post-treated and column-separated to give a corresponding product 4 h (yield: 86%).

Example 9

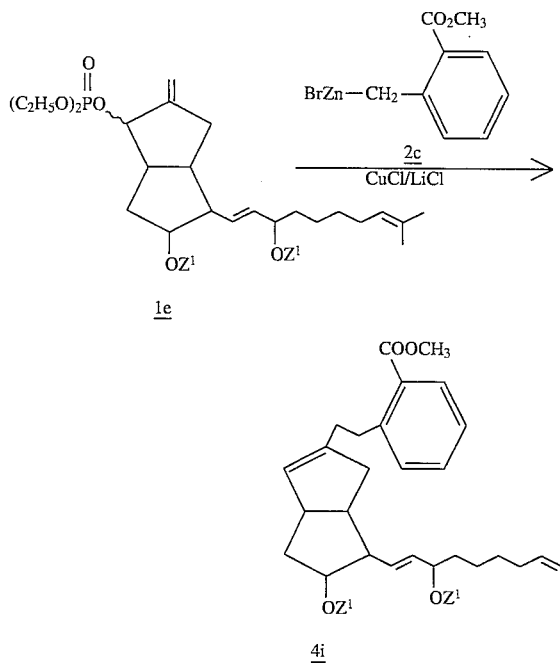

4i

A reaction of a reactant 1e (1 mmol) with a zinc compound (10 mmol) prepared from methyl-2-(bromomethyl)benzoate (10 mmol) was carried out in the presence of CuCl (10 mmol) and LiCl (20 mmol) in the same manner as in Example 2. The reaction mixture was post-treated and column-separated to give a corresponding product 4i (yield: 86%).

Example 10

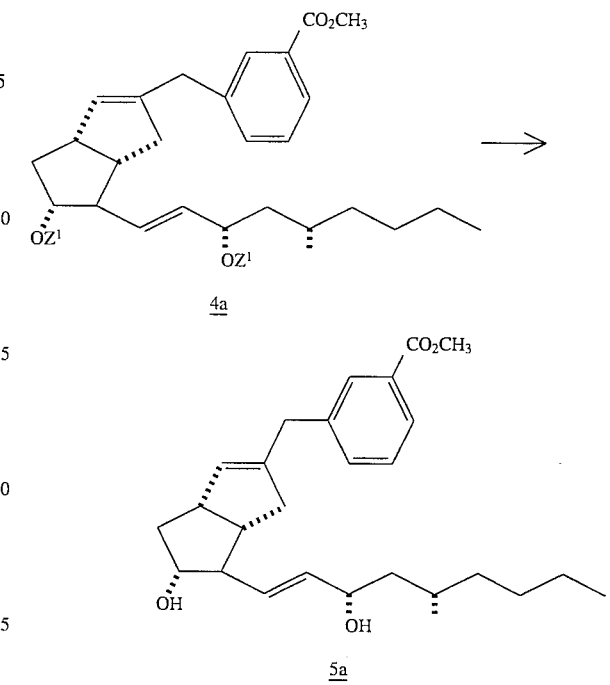

5a

A disilyl compound 4a (950 mg, 1.45 mmol) was dissolved in 10 ml of THF, the mixture was stirred with ice cooling, and 6 ml (2.0 equivalent) of a 1M THF solution of tetrabutylammonium fluoride was added. The mixture was warmed to 30° C., and stirred for 5 hours. The reaction solvent, THF, was distilled off under reduced pressure, a saturated ammonium chloride aqueous solution and ethyl acetate were added to the concentrate, and the mixture was subjected to extraction. An organic layer was washed with a saturated sodium chloride aqueous solution, and dehydrated and dried over anhydrous magnesium sulfate, and the solvents were distilled off under reduced pressure to give a concentrate. The concentrate was subjected to silica gel chromatography (n-hexane:ethyl acetate=1:1–1:2) for separation and purification to give 586 mg (95%) of a diol 5a.

$^1$H-NMR (CDCl$_3$, ppm) δ; 7.85 (2H,m), 7.35(2H,m), 5.40(2H,m), 5.30(1H,d,J=1.2 Hz), 4.10(1H,m), 3.90(3H,s), 3.70(1H,m), 3.38(2H,bs), 3.00(1H,m), 2.40–2.20(3H,m), 1.95–1.80(2H,m), 1.40–1.10(12H,m), 0.85(6H,s).

IR (liquid film) cm$^{-1}$: 3364, 2955, 2920, 2872, 1725, 1607, 1590, 1446, 1435, 1281, 1200, 1105, 1088, 995, 970, 756, 704, Mass m/e: 408(M-18)$^+$ UV λC$_2$H$_5$OH max nm (log ε): 231.6nn (3.94).

Examples 11–18

In the same manner as in Example 10, reactants 4b, 4c, 4d, 4e, 4f, 4g, 4h and 4i in an amount of 1 mmol each were respectively dissolved in 10 ml of THF, each mixture was stirred with ice cooling, and 4 ml (2.0 equivalent) of a 1M THF solution of tetrabutylammonium fluoride was added to each mixture. Each mixture was warmed to 30° C., and stirred for 5 hours. The reaction mixtures were treated in the same manner as in Example 10, and the resultant crude products were subjected to silica gel chromatography (n-hexane:ethyl acetate=1:1–2:1) for separation and purification to give corresponding diol compounds 5b, 5c, 5d, 5e, 5f, 5g, 5h and 5i at yields shown in Table 5.

TABLE 5

| Example | Reactant | Product | Yield (%) |
|---|---|---|---|
| 11 | 4b | 5b | 94 |
| 12 | 4c | 5c | 92 |
| 13 | 4d | 5d | 96 |
| 14 | 4e | 5e | 95 |
| 15 | 4f | 5f | 94 |

TABLE 5-continued

| Example | Reactant | Product | Yield (%) |
|---|---|---|---|
| 16 | 4g | 5g | 92 |
| 17 | 4h | 5h | 94 |
| 18 | 4i | 5i | 88 |

Table 6 shows the physical property values of the compounds 5b, 5c, 5d, 5e, 5f, 5g, 5h and 5i.

TABLE 6

| Compound | $^1$H-NMR (CDCl$_3$, ppm) δ | IR (liquid film) cm$^{-1}$ | UV λC$_2$H$_5$OH max nm (log ε) | | Ms |
|---|---|---|---|---|---|
| 5b | 7.95(2H, d, J=7.5Hz), 7.25(2H, d, J=7.5Hz), 5.50(2H, m), 5.30(1H, d, J=1.2Hz), 3.90(3H, s), 3.75(1H, m), 3.00(1H, m), 2.80(2H, t, J=8Hz), 2.40-1.20(18H, m), 1.15(3H, s), 0.90(3H, t) | 3380, 2953, 2932, 2872, 1723, 1611, 1455, 1435, 1310, 1281, 1192, 1179, 1113, 1021, 909, 768, 733, 708 | 239.2 nm, (4.16) | 208.6 nm (4.04) | M$^+$ = 426(No detct.) M/e = 408 = M$^+$H$_2$O |
| 5c | 7.85(2H, m), 7.40(2H, m), 5.45(2H, m), 5.30(1H, d, J=1.2Hz), 3.90(3H, s), 3.75(1H, m), 3.40(2H, bs), 3.00(1H, m), 2.40-1.15(16H, m), 1.10(3H, s), 0.90(3H, t) | 3384, 2955, 2932, 2872, 1725, 1607, 1590, 1447, 1439, 1379, 1283, 1200, 1107, 1090, 992, 974, 758 | — | — | M$^+$ = 412(No detct.) M/e = 394 = M$^+$H$_2$O |
| 5d | 7.85(2H, m), 7.38(2H, m), 5.50(2H, m), 5.30(1H, d, J=1.2Hz), 4.05(1H, m), 3.90(3H, s), 3.75(1H, m), 3.38(2H, bs), 3.00(1H, m), 2.40-1.15(16H, m), 0.85(3H, t) | 3370, 2923, 1720, 1701, 1445, 1438, 1307, 1281, 1202, 1113, 1086, 972, 760 | 231.6 nm, (3.94) | 211.2 nm (3.97) | |
| 5e | 7.95(2H, d, J=7.50Hz), 7.25(2H, d, J=7.5Hz), 5.55(2H, m), 5.32(1H, d, J=1.2Hz), 4.18(1H, m), 3.90(3H, s), 3.75(1H, m), 3.00(1H, m), 2.80(2H, t, J=8Hz), 2.40-1.20(19H.m), 0.90(6H.m) | 3400, 3335, 2955, 2928, 1728, 1723, 1717, 1705, 1611, 1456, 1485, 1416, 1377, 1310, 1192, 1179, 1111, 1021, 968, 911, 856, 768, 733 | 238.8 nm, (4.07) | 209.0 nm (3.95) | M$^+$ = 440(No detct.) M/e = 422 = M$^+$H$_2$O |
| 5f | 7.95(2H, d, J=10Hz), 7.36(2H, d, J=7.5Hz), | 3524, 3425, 2953, 2928, 2863, 1720, | 239.2 nm, | 210.2 nm | |

TABLE 6-continued

| Compound | ¹H-NMR (CDCl₃, ppm) δ | IR (liquid film) cm⁻¹ | UV λC₂H₅OH max nm (log ε) | Ms |
|---|---|---|---|---|
| | 5.55(2H, m), 5.30(1H, d, J=1.2Hz), 4.05(1H, m), 3.90(3H, s), 3.75(1H, m), 3.00(1H, m), 2.80(2H, t, J=8Hz), 2.40–1.15(18H, m), 0.90(3H, t) | 1701, 1610, 1437, 1416, 1285, 1194, 1179, 1113, 1086, 1020, 972, 766 | (3.92)   (3.80) | |

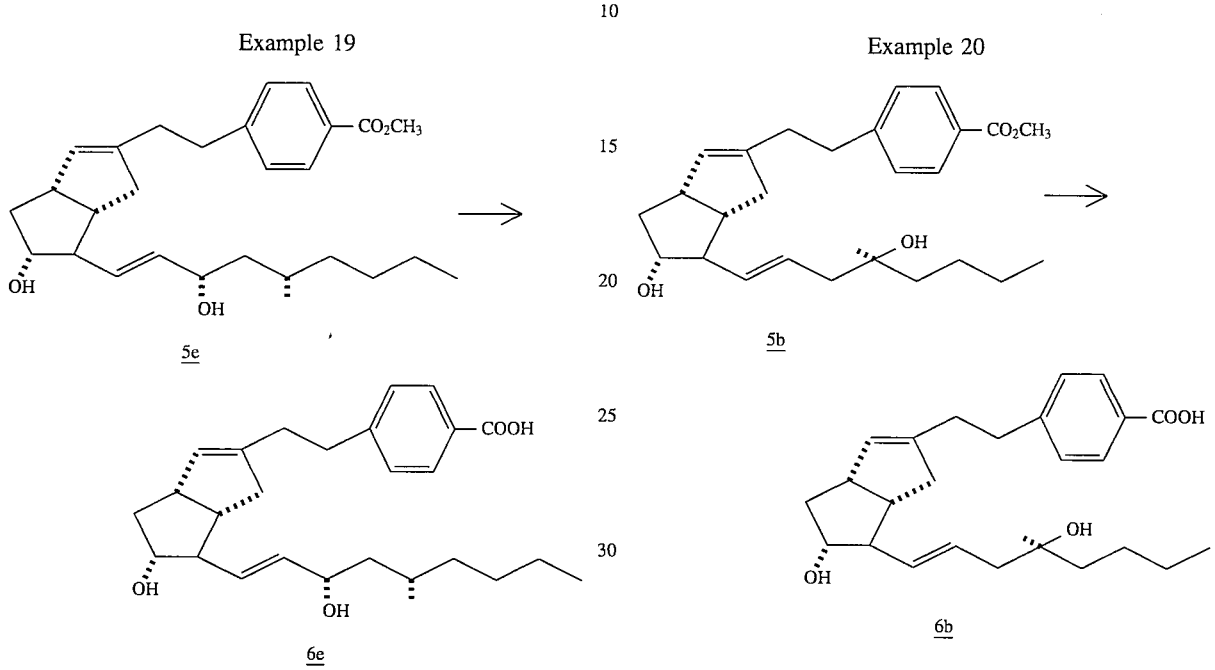

A diol 5e in an amount of 67.5 mg (0.15 mmol) was dissolved in 6 ml of THF at room temperature, an alkali aqueous solution of 40 mg (0.95 mmol) of LiOH.H₂O and 3 ml of H₂O was dropwise added to the THF solution with stirring, and the mixture was further stirred for 26 hours to show that the starting materials disappeared on TLC [hexane:ethyl acetate=1:4]. Added to the liquid mixture was 2 ml of 1N-HCl, and the mixture was stirred for 30 minutes. A saturated sodium chloride aqueous solution and ethyl acetate were added, and the mixture was subjected to extraction. An organic layer was rewashed with a saturated sodium chloride aqueous solution, dehydrated and dried over anhydrous magnesium sulfate, and the solvent was distilled off under reduced pressure. The resultant concentrate was subjected to silica gel chromatography [hexane:ethyl acetate=1:2–1:4 (containing 0.1% acetic acid] for separation and purification to give 57 mg (89%) of a carboxylic acid 6e.

¹H-NMR (CDCl₃, ppm) δ; 8.00 (2H,d,J=7.5 Hz), 7.25(2H,d,J=7.5 Hz), 6.00(3H,bs), 5.45(2H,m), 5.25(1H,d, J=1.2 Hz), 4.15(1H,m), 3.7(1H,m), 3.00(1H,m), 2.75(2H,t, J=7.5 Hz), 2.40–1.80(7H,m), 1.45–1.20(10H,m), 0.85(6H, m).

IR (liquid film) cm⁻¹: 2955, 2924, 2872, 1692, 1613, 1424, 1318, 1289, 1179, 1090, 1015, 968, 839, 762, 708, 673

Mass m/e: 408(M-H₂O)⁺

UV λC₂H₅OH max nm (log ε): 237.8(4.38), 207.8(4.29).

A hydrolysis of 100 mg (0.24 mmol) of a reactant 5b was carried out in the same manner as in Example 19. The reaction product was post-treated and column-purified to give 91 mg (96%) of a corresponding carboxylic acid 6b. 1H-NMR (CD30D, ppm) δ; 8.00(2H,d,J=7.5 Hz), 7.25( 2H, d,J=7.25Hz ), 6.00(3H,bs), 5.55(1H,m), 5.42(1H,m), 5.25(1H,d,J=1.2 Hz), 3.75(1H,m), 3.00(1H,m), 2.80(2H,t,J= 10 Hz), 2.60–1.80(9H,m), 1.50–1.20(7H,m), 1.15(3H,s), 0.90(3H,t).

IR (liquid film) cm⁻¹: 2956, 2930, 2915, 2842, 2664, 1682, 1611, 1576, 1455, 1424, 1320, 1291, 1179, 1090, 972, 847, 762, 706, 677

Mass m/e: 394 (M-H₂)⁺

UV λC2H5OH max nm (log ε): 237.8 (4.16), 208.0 (4.08).

Example 21

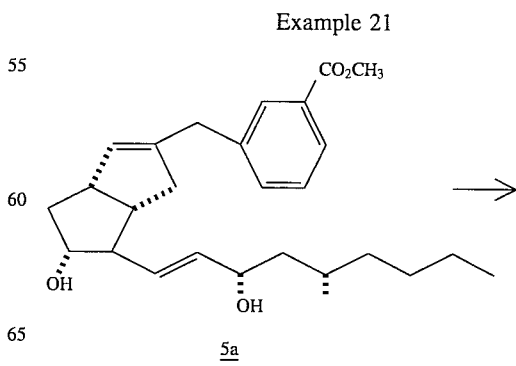

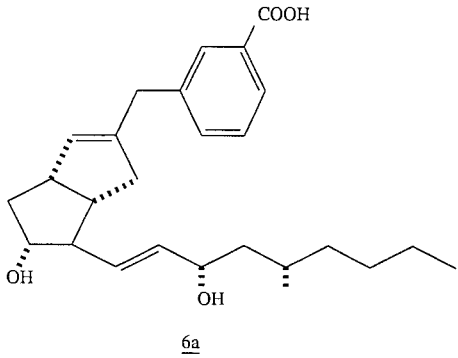

6a

A hydrolysis of 190 mg (0.446 mmol) of a reactant 5 was carried out in the same manner as in Example 19. The reaction product was post-treated and column-purified to give 184 mg (100 %) of a corresponding carboxylic acid 6a.

1H-NMR (CD$_3$OD, ppm) δ; 7.85 (2H,m), 7.40(2H,m), 5.65–5.30 (3H, m), 4.05(1H,m), 3.75(1H,m), 3.4(2H,bs), 3.30(1H,m), 3.00(1H,m), 2.40–2.15(17H,m), 0.85(6H,m).

Mass m/e: 394(m-H$_2$O)$^+$

IR (liquid film) cm$^{-1}$: 3360, 2957, 2928, 2645, 1696, 1607, 1589, 1453, 1412, 1377, 1279, 1196, 1086, 997, 970, 839, 816

UV λC$_2$H$_5$OH max nm (log ε):

229.6 (3.94), 213.0 (3.95)

UV (CH$_3$OH) λmax 229.6 nm log ε 3.94 λmax 213.0 nm log ε 3.95.

Examples 22–24

A hydrolysis of 1 mmol of each of reactants 5 d, 5 f and 5 g was carried out in the same manner as in Example 19. The reaction products were post-treated and column-purified to give corresponding carboxylic acids 6, 6 f and 6 g at yields shown in Table 7.

TABLE 7

| Example | Reactant | Product | Yield (%) |
|---|---|---|---|
| 22 | 5g | 6g | 90 |
| 23 | 5d | 6d | 96 |
| 24 | 5f | 6f | 95 |

Table 8 shows the physical property values of the compounds 6d, 6f and 6g.

TABLE 8

| Compound | $^1$H-NMR (CD$_3$OD, ppm) δ | IR (liquid film) cm$^{-1}$ | UV λC$_2$H$_5$OH max nm (log ε) | |
|---|---|---|---|---|
| 6g | 7.85(2H, m), 7.35(2H, m), 5.60-5.30(3H, m), 4.10(1H, m), 3.70(1H, m), 3.38(2H, bs), 3.00(1H, m), 2.50-1.10(18H, m) | 3300, 2955, 2920, 1720, 1607, 1590, 1255, 1100, 1000, 970, 835, 770 | — | — |
| 6d | 7.85(2H, m), 7.35(2H, m), 5.55-5.25(3H, m), 4.95(2H, m), 4.20(1H, m), 3.90(1H, m), 3.65(1H, m), 3.40(2H, bs), 3.00(1H, m), 2.40-1.15(15H, m), 0.85(3H, t) | 3300, 2957, 1733, 1717, 1700, 1609, 1590, 1456, 1194, 968, 752 | 229.6 nm (3.97) | 215.0 nm (3.95) |
| 6f | 7.95(2H, d, J=7.5Hz), 7.30(2H.d, J=7.5Hz), 5.55(2H, m), 5.30(1H.d, J=1.2Hz), 4.00(1H, m), 3.70(1H, m), 2.95(1H, m), 2.80(2H, t, J=8Hz), 2.45-1.15(18H, m), 0.85(3H, t) | 3325, 2928, 1734, 1717, 1698, 1684, 1636, 1589, 1490, 1456, 1420, 1339, 1293, 1179, 1084, 972, 853 | 238.0 nm (4.09) | 208.6 nm (3.94) |

Example 25

Measurement of the activity for inhibiting the DNA synthesis of human smooth muscle cells:

Cultured cells (at the 5th passage) of blood vessel smooth muscle cells (supplied by Kurabo Ltd.), from normal human aorta were inoculated in a 96-well plate (supplied by Corning) in a cell density of 3×10$^3$ cells/well, and cultured for 3 days. The medium was changed from a growth medium (SGM: supplied by Kurabo) to a basal medium (SGM: supplied by Kurabo Ltd), and the cells were cultured for 24 hours. Growth media (SGM) containing solutions of the compounds obtained in Examples 10, 11, 12, 14, 19 and 20 in ethanol (supplied by Wako) were added to the culture. After 16 hours, 3H-thymidine (supplied by Amersham) was added in an amount of 0.5 μCi/well, and after 8 hours, the mixtures were frozen at –20° C. Then, the plate was placed under room temperature to melt the mixtures, and the 3H-thymidine incorporated into nucleus was adsorbed on glass filters with a cell harvester (supplied by Labo Science). Then, the filters were respectively placed in a toluene scintillater solution (supplied by Wako), and the 3H-thymidine was counted with a liquid scintillation counter (supplied by Hewlett Packard).

FIG. 1 shows the results. In FIG. 1, the axis of ordinates shows amounts of $^3$3H-thymidine incorporated into nucleus, and the axis of abscissae shows added samples and the concentrations of the samples. The statistical processing was effected by a student's test, and P values were expressed by asterisk marks.

FIG. 1 shows that all the compounds 5e, 6e, 5b, 6b, 5a and 5c of the present invention has the activity for inhibiting the proliferation of human smooth muscle cells.

We claim:

1. α-Chain-modified isocarbacyclins of the following formula (1),

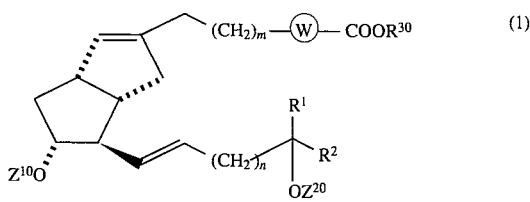

wherein (W) is a phenylene group, a C$_3$–C$_7$ cycloalkylene group or a thiophendiyl group R$^1$ is a hydrogen atom, a methyl group, an ethyl group or a vinyl group;

R$^2$ is a linear or branched C$_3$–C$_8$ alkyl group, alkenyl group or alkynyl group or a C$_3$–C$_7$ cycloalkyl group;

R$^{30}$ is a hydrogen atom, a C$_1$–C$_{10}$ alkyl group, a phenyl group, a benzyl group, a naphthyl group or one equivalent of a cation;

each of Z$^{10}$ and Z$^{20}$ is independently a hydrogen atom, tri(C$_1$–C$_7$ hydrocarbon)silyl group or a group which forms an acetal bond or an ester bond together with an oxygen atom to which it bonds;

n is 0 or 1; and m is an integer of 0 to 4.

2. The α-Chain-modified isocarbacyclins of claim 1, wherein (W) in the above formula (1) is a phenylene group.

3. The α-Chain-modified isocarbacyclins of claim 1, wherein, in the above formula (1), R$^{30}$ is a hydrogen atom, a C$_1$–C$_4$ alkyl group or one equivalent of a cation; and Z$^{10}$ and Z$^{20}$ are hydrogen atoms.

4. A process for the production of α-chain-modified isocarbacyclins of the following formula (1),

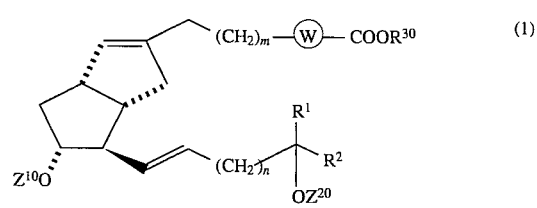

wherein (W), R$^{30}$, R$^1$, R$^2$, Z$^{10}$, Z$^{20}$, m and n are as defined below, which comprises reacting 2,6,7-trisubstituted-3-methylenebicyclo[3.3.0]octanes of the following formula (2),

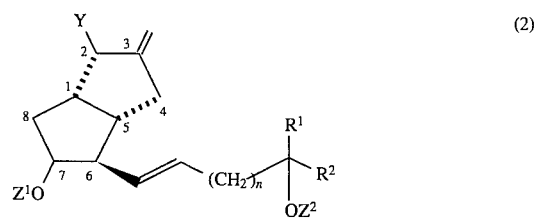

wherein

Y is a group of $$(R^3O)_2\underset{\underset{B}{|}}{P}-A- \text{ or } R^4O\underset{\underset{O}{\|}}{C}O-$$

(in which each of $R^3$s is independently a $C_1$–$C_6$ hydrocarbon group, A and B are both oxygen atoms or one is an oxygen atom and the other is a sulfur atom, and $R^4$ is a $C_1$–$C_6$ hydrocarbon group);

$R^1$ is a hydrogen atom, a methyl group, an ethyl group or a vinyl group;

$R^2$ is a linear or branched $C_3$–$C_8$ alkyl group, alkenyl group or alkynyl group, or a $C_3$–$C_7$ cycloalkyl group;

each of $Z^1$ and $Z^2$ is independently a tri($C_1$–$C_7$ hydrocarbon)silyl group or a group which forms an acetal bond or an ester bond together with an oxygen atom to which it bonds; and n is 0 or 1, with an organic zinc compound of the following formula (3), $$X^1Zn-(CH_2)_m-(W)-COOR^3 \qquad (3)$$

wherein $R^3$ is a $C_1$–$C_{10}$ alkyl group, a phenyl group, a benzyl group or a naphthyl group;

(W) is a phenylene group, a $C_3$—$C_7$ cycloalkylene group or a thiophendiyl group;

$X^1$ is a halogen atom, and m is an integer of 0 to 4, in the presence of a cuprous salt of the following formula (4), $$CuX^2 \qquad (4)$$

wherein $X^2$ is a cyano group or a halogen atom, optionally subjecting the reaction product to a deprotection reaction and further optionally subjecting the reaction product to a salt-forming reaction.

* * * * *